Oct. 3, 1967 H. KERRIGAN Plant Pat. 2,770
AZALEA PLANT
Filed June 7, 1966
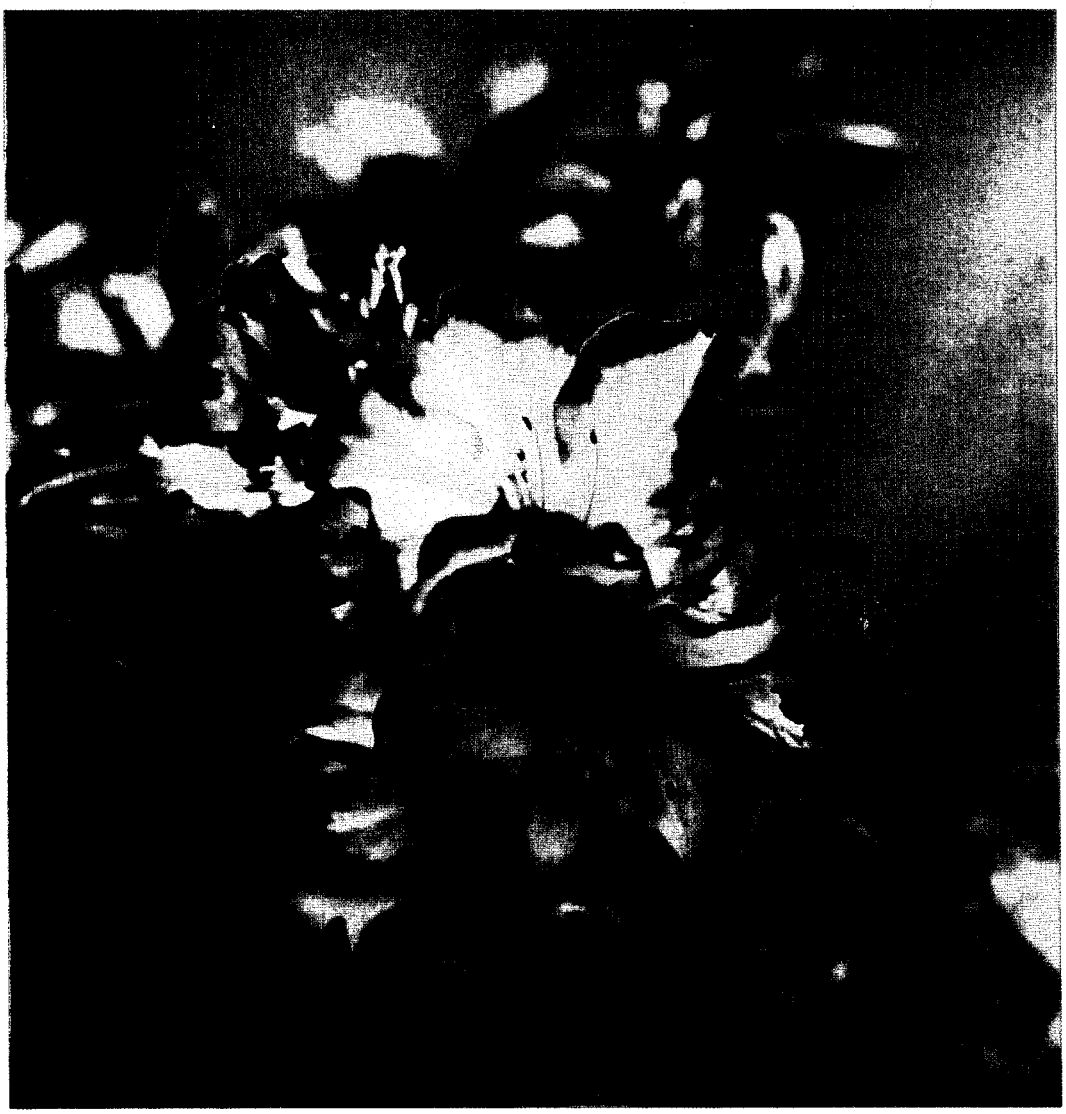

United States Patent Office

Plant Pat. 2,770
Patented Oct. 3, 1967

2,770
AZALEA PLANT
Howard Kerrigan, 3003 Totterdell St.,
Oakland, Calif. 94611
Filed June 7, 1966, Ser. No. 555,925
1 Claim. (Cl. Plt.—55)

The invention relates to a new and distinct variety of azalea plant of the Belgain Indica type, originated by me in 1954 as a consequence of a breeding program begun in 1943. The parentage of my new azalea plant is as follows:

Albert-Elizabeth, the seed parent × Captain Blood, the pollen parent.

The object of the cross was to produce a plant with more vigor and strength of stem than the variety Albert-Elizabeth with the same flower color pattern plus the intensity of color developed by Captain Blood. These objectives were achieved along with other desirable improvements, as evidenced by the following unique combination of characteristics which are oustanding in the new variety and which distinguish it from its parents as well as from all other varieties of which I am aware. My new variety is primarily characterized by:

A unique combination of red and white color in the same flower in which the edge of the corolla is deep red and the ground color pure white with little or no bleeding at the boundary of the two colors, combined with a ruffled hose-in-hose corolla, strong, vigorous growth, and ease of propagation and culture.

Asexual reproduction of my new variety by cuttings, through a series of annual propagations at Oakland, Calif. shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of own rooted plants produced and grown under average conditions in greenhouse at Oakland, Calif. from 1954 to 1965.

Plant large, robust, ascending, spreading, 30″ high and 40″ across at maturity. Branches stout but supple, gently arching. Basal shoots vigorous, about 3/16″ in diameter; axillary branches about 3/32″ the first season. Internodes of basal shoots about 5/16″ long. Stems erect, light green when young, becoming rufous to brown when old, bark more or less conspicuously straited, young stems bearing prominent chestnut strigae which become black with age, persistent, bleaching to light tan the second year.

Foliage evergreen, of two size classes. Leaves of vigorous growth about 2⅝″ long by 1¼″ wide, petiolate, the petioles about ½″ long, lamina slightly decurrent, descending the petiole up to 3/16″, ovate; the margin is entire, sparsely ciliate, the cibia small, inconspicuous. The apex is mucronate. The midrib is pubescent, especially below. The trichomes are flat, lanceolate, slender up to 3/32″ in length, conspicuous, black, abundant on the lower surface, smaller, sparser, and chestnut brown on the upper surface of the midrib. The lamina is sparsely pubescent above and below. The trichomes are extremely slender, black or chestnut, and inconspicuous.

Leaves of the branches from older wood smaller, about 1¼″ long by 11/16″ wide with proportionately smaller trichromes but otherwise similar to the larger leaves. The color of the leaves is light spinach green below (0960/3) and dark spinach green above (0960/1) to (0960).

The bud of the inflorescence is light green. The scales are small, cuculate at anthesis. Pubescence is sparse, small, black to brown essentially restricted to the rib. The scales become scarious with sub-hyaline margins at dehiscence. Mature scales are about 7/16″ long x ⅜″ wide, heart shaped. The inflorescence is 2–3 flowered. The flowers are borne in an umbellate corymb. One flower of three flowered inflorescences matures several days later than the more precocious pair and has a shorter peduncle. The peduncles are short, stout about ⅛–¼″ long x 3/32″ wide, moderately pubescent, light green to nearly white, pinkish where exposed to sunlight. Pubescence is moderately dense, hyaline with pink bases, short, silky. Calyx corolliform, five lobed, sepals imperfect, ragged. Tube of calyx about ½″ deep x ⅝″ across, broadly flared, lightly fluted. Lobes about ⅝″ wide by 1″ long highly variable as to shape and size, secondarily lobed and incised. The margins of the lobes are long ciliate. Dorsal lobes freckled chartreuse and adjacent tissues are tinted greenish. The reverse of the midribs are stained pink over the white ground color. Margins spotted and splotched China Rose. The corolla is showy, white, edged with bright rich China Rose (024), sharply delineated from the ground color on both the reverse and obverse. The China Rose edging is about ⅛–3/16″ wide. The tube is about ⅝″ long by ⅞″ across at the throat, flaring, bilaterally symmetrical, slightly gibbous, somewhat higher than broad, more or less prominently fluted with the midveins raised. The five corolla lobes are of two size classes. The ventral two larger about ¾–1″ across by 1–1⅛″ deep, auriculate, auriculae small, not edged China Rose (024). The dorsal three lobes are smaller, about 15/16″–1″ across by ⅞″–1 1/16″ long. The flower is about 2¼″–2⅝″ across by 1⅜″–1½″ deep. The dorsal lobes and throat are freckled chartreuse.

The stamens are five, filaments slender, light crimson (22/2), 1–1⅜″ long sometimes pelataceous and staminoidal. Anthers small, tan about 1/32 x 3/32″, pollen white to ivory. The pistil is short about ¾″–⅞″ long, stigma tan, capitate, barely broader than the style, five lobed, receptive surface divided into five sections, style stout, ¾″ long, barely curved, not sigmoid, conspicuously expanded at the base to nearly the diameter of the ovary about 11/16–3/32″ in diameter at base, 1/32″ at middle. The thickened basal portion of the style densely pubescent, pubescence long, silky, hyaline. Ovary about ⅛″ long and ⅛″ across, heavily pubescent, the pubescence dense, long, silky, hyaline. Basal cell of the trichome crimson.

Having thus disclosed my invention, I claim:

A new and distinct variety of azalea plant of the Belgian Indica type substantially as herein shown and described primarily characterized by: a unique combination of red and white color in the same flower in which the edge of the corolla is deep red and the ground color pure white with little or no bleeding at the boundary of the two colors, combined with a ruffled hose-in-hose corolla, strong, vigorous growth, and ease of propagation and culture.

No references cited.

ABRAHAM G. STONE, *Primary Examiner.*
ROBERT E. BAGWILL, *Examiner.*